United States Patent [19]
Larose et al.

[11] Patent Number: 5,723,406
[45] Date of Patent: Mar. 3, 1998

[54] METHOD FOR CONTROL OF HORTICULTURE DISEASES, AND DECONTAMINATION OF PLANT TISSUE

[76] Inventors: Rene N. Larose, 69 Butler Dr., Glastonbury, Conn. 06033; Michael N. Abbot, 49 Oak St., Windsor Locks, Conn. 06096

[21] Appl. No.: 581,863

[22] Filed: Jan. 2, 1996

[51] Int. Cl.$^6$ .............................. A01N 3/02; A01N 37/02; A01N 59/00
[52] U.S. Cl. .................... 504/114; 424/605; 424/616; 47/58; 47/DIG. 3
[58] Field of Search .................................. 424/605, 616; 47/58, DIG. 3; 504/114

[56] References Cited

U.S. PATENT DOCUMENTS

| | | | |
|---|---|---|---|
| 3,912,490 | 10/1975 | Boghosian | 71/28 |
| 4,354,327 | 10/1982 | Smeltzer et al. | 47/58 |
| 4,863,688 | 9/1989 | Schmidt et al. | 422/28 |
| 4,917,815 | 4/1990 | Beilfuss et al. | 252/186.23 |
| 5,168,655 | 12/1992 | Davidson et al. | 47/62 |

*Primary Examiner*—S. Mark Clardy
*Attorney, Agent, or Firm*—Robert S. Smith

[57] ABSTRACT

A method for control of horticulture diseases and decontamination of plant tissue which includes applying a solution of hydrogen peroxide to plant tissue, said hydrogen peroxide being a solution having a concentration of between 0.05 to 3.00%. In some cases the hydrogen peroxide solution has a concentration of between 0.05 and 1.5%. Some forms of the invention may utilize a hydrogen peroxide solution that further includes an acid selected from the group consisting of acetic acid and phosphoric acid. Various structures are used for applying the hydrogen peroxide solution such as hydraulic spraying, misting, fogging, or injecting the hydrogen peroxide into a commercial cooling system. In other cases the hydrogen peroxide solution is injected into a recirculating subirrigation nutrient system solution to control microbial growth in the irrigation water. In some cases the hydrogen peroxide solution is applied to the plant tissue at a variety of stages in the plant production cycle. Other application of the invention include applying misting the hydrogen peroxide solution over terminal stem cuttings until they reach root sufficiency. The invention also includes the method of eradicating insects which includes applying a solution of hydrogen peroxide to the environment of the insects and the method of treating water to reduce the presence of fungi present in the water which includes applying hydrogen peroxide to the water.

27 Claims, No Drawings

METHOD FOR CONTROL OF HORTICULTURE DISEASES, AND DECONTAMINATION OF PLANT TISSUE

BACKGROUND OF THE INVENTION

This invention relates generally to the sanitization of living plant tissue and more specifically to a safe and effective sanitization method which results in a significant decrease in the incidence of plant diseases and hence increased plant quality. The invention has application to horticulture products generally including cultivated and wild plants and cut flowers. The description that follows will be understood to use the term "plant" to refer to all living plant tissue. Other aspects of the invention relate to water treatment.

Most plant tissue infectious diseases are caused by viruses, bacteria, fungi, lower plant forms such as algae, or insects. Most often disease control involves the integrated use of several methods and compounds. Rarely is disease control achieved by a single procedure. The five fundamental principles of disease control are:

1. Exclusion: Preventing pathogens from entering and becoming established in uninfected gardens, fields and greenhouses.
2. Eradication: Elimination of the pathogens once they have become established on plants.
3. Protection: Interposition of a protective barrier between the susceptible host and the pathogen, usually by protective sprays.
4. Resistance: The development and use of genetic mutation.
5. Therapy: The treatment of plants with something that will inactivate or inhibit the pathogen.

Commercial production of plants, either for agriculture or ornamental horticulture, in a controlled environment or in field production is susceptible to contamination by microorganisms which can adversely affect plant growth, survival rates and plant quality during all stages of the plant life cycle. Some microorganisms which are known to adversely affect plant growth and development are Alternaria, *Botrytis cinerea*, Fusarium, Anthracnose, Powdery Mildew, and Rust. In order to produce healthy plants suitable for human consumption and commercial sale it is essential that a program be developed and implemented to inhibit the growth of these microorganisms. Without such a program the unchecked growth of microorganisms can have a devastating effect on plant quality and the number of plants that can be sold.

Most farms, ornamental horticulture nurseries, and greenhouses utilize fungicides, bactericides, insecticides and/or viricides to inhibit the growth of microorganisms. This treatment is necessary to achieve a high level of plant quality and maximize the number of plants that can be sold. Often these products are applied to the plant tissue as a spray, mist, fog, drench, dip, dust or granular. The apparatus use for application includes high pressure sprayers, dusters, aerosol generators, misters, cold foggers, thermal foggers, overhead and/or drip irrigation equipment and flooding benches.

A major consideration, particularly in the production of ornamental plants, is that considerable effort must be placed on preventing fungi because once the fungus develops the leaves are quickly damaged and this will affect the aesthetics of the plant. This will permanently and dramatically affect the commercial value of the plant because all customers prefer a perfect plant. Thus, the typical commercial grower will invest a considerable amount of time and money in preventive procedures. One powerful and common treatment was marketed with the trademark "Benlate." This material was taken off the market because of a herbicide contamination of the available supply and the need for renewed governmental approval of the decontaminated substance. No substitute was ever placed on the market. A similar scenario has affected other chemicals that have been used in the growing of plants. At least in some cases the products have been taken off the market either because of product liability exposure or governmental requirements.

While the use of these chemicals does reduce the levels of microorganisms on the plant tissue there are several issues which make those chemicals increasingly more difficult to use. These issues are: First, the public health concerns related to worker exposure to potentially dangerous chemicals during and after the preparation and application of the chemical as well as consumer exposure to chemical residue on the plant material. Second, government regulations often restrict personnel access up to 72 hours after chemical applications have occurred This limits worker productivity and increases the cost of applying chemical treatments. Third, the residual odor after the application of chemicals creates an unpleasant working environment for the farm, ornamental horticulture nursery, or greenhouse. Fourth, the dried residue of the chemical on the finished plant products can cause an unsightly plant appearance render the plants unsalable Fifth, there is the possibility of a phytotoxic response by some plants to some chemicals which can cause disfiguring, stunting, defoliation, or even death of the plant that is exposed. Lastly, many of the chemicals currently being used to inhibit the growth of microorganisms on plant tissue face the possibility of more stringent government regulations in the future.

Because of the difficulties now facing the current methods of inhibiting the growth of microorganisms on living plant tissue, a need exists for a safe and effective disinfectant for use on commercially produced plant material.

An object of the present invention is to provide a safe method for the decontamination of growing plants from fungal and microbial plant pathogens.

It is an another object of the present invention to provide a method which will decrease microbial contamination of living plant tissue without adversely affecting plant growth.

Still another object of the present invention to provide a method for disinfecting to living plant tissue that is safe and convenient to use.

It is another object of the present invention to provide a method for disinfecting living plant tissue which reduces worker exposure to hazardous chemicals.

It is yet another object of the present invention to provide a method of protecting plant tissue to microbial infestation throughout the plant life cycle.

Still another object of the invention is to provide a method that will also serve as an insecticide in many applications.

Another object of the invention is to provide a safe treatment for water, such as in ornamental pools, that will not be injurious to fish disposed in the pool.

SUMMARY OF THE INVENTION

It has now been found that these and other objects of the invention may be attained in a method for control of horticulture diseases and decontamination of plant tissue which includes applying a solution of hydrogen peroxide to plant tissue, said hydrogen peroxide being a solution having a concentration of between 0.05 to 3.00%.

In some cases the hydrogen peroxide solution has a concentration of between 0.05 and 1.5%. Some forms of the invention may utilize a hydrogen peroxide solution that further includes an acid selected from the group consisting of acetic acid and phosphoric acid.

Various structures are used for applying the hydrogen peroxide solution such as hydraulic spraying, misting, fogging, or injecting the hydrogen peroxide into a commercial cooling system. In other cases the hydrogen peroxide solution is injected into a recirculating subirrigation nutrient system solution to control microbial growth in the irrigation water.

In some cases the hydrogen peroxide solution is applied to the plant tissue at a variety of stages in the plant production cycle. Other application of the invention include applying misting the hydrogen peroxide solution over terminal stem cuttings until they reach root sufficiency.

The invention also includes the method of eradicating insects which includes applying a solution of hydrogen peroxide to the environment of the insects and the method of treating water to reduce the presence of fungi present in the water which includes applying hydrogen peroxide to the water.

DESCRIPTION OF THE PREFERRED EMBODIMENT

The method in accordance with the invention utilizes hydrogen peroxide, sometimes known as peroxygen, for the purpose of killing the most common plant pathogens in greenhouses, lawns, gardens, orchards, forests, and other agricultural crops. It was discovered that when a dilute solution of hydrogen peroxide is applied to living plants by spray, mist, fog or immersion (including the root system), the plant pathogens present on the surfaces were either totally eradicated or substantially reduced. The plants suffered no adverse affects from the treatment. Daily treatments with hydrogen peroxide had no adverse effect upon the health of the plants. There were no signs of discoloration of the flowers on ornamental plants. The most obvious effect was the elimination of the fungi, particularly on the plant leaves and stems since fungi are extremely visible on these areas. The effect of the hydrogen peroxide upon pathogenic bacteria and viruses were not observed since these diseases are relatively uncommon. However, the effects of hydrogen peroxide upon bacteria and viruses has been well documented in the literature and one could expect the same sanitizing effect upon these agents as was observed upon the more resistant fungal agents. The important point to remember is that hydrogen peroxide is a very powerful disinfectant and yet does not harm delicate plant tissues when used at a concentration lethal to the plant pathogens. Other added advantages of hydrogen peroxide disinfection are, the lack of a residue upon the treated surfaces, and the totally innocuous breakdown products of water and oxygen which are readily absorbed by the plants.

Still another surprising advantage of the application of even the moderate concentration of hydrogen peroxide that will not harm delicate plant tissue is that this moderate concentration will substantially reduce the population of insects in the plant environment.

Since insects are a source of plant diseases and even the presence of insects on plants make the plant unsuitable for sale. Plants having an infestation of insects are even worse than being unsuitable for sale in that if any such plants were to reach any retail or wholesale customer for such plants it is unlikely that the customer will quickly purchase any additional plants from the same supplier.

The invention may usually be attained in a method in which a hydrogen peroxide solution of between 0.05% and 3.0% is applied periodically to the plant material throughout the plant production cycle. The method permits the hydrogen peroxide solution to be applied to the plant material continuously and or periodically during this time period without adversely affecting the plant growth.

More particularly, a solution of hydrogen peroxide diluted with water to a total hydrogen peroxide concentration of about 0.05 to 3.00 percent is preferred. A solution of about 1.0% hydrogen peroxide is preferred for initial application to plant tissue already infected with microorganism while a solution of about 0.05% is preferred for repeated applications intended to protect plant tissue from microbial infection. The addition of acetic or phosphoric acid to the solution at a concentration of about 0.05% is useful to stabilize the hydrogen peroxide solution in certain water conditions. Any commercial source of hydrogen peroxide solution may be used to carry out the method of the present invention. Typical concentrations commercially available are between 3 and 70 percent hydrogen peroxide. While any of these forms will work in the present invention, it may be more convenient in some cases to purchase a 50% concentration and then dilute that solution down to the appropriate concentration in accordance with the present invention. One method which may be useful for diluting concentrated solutions is to use a Dosatron Proportioner made by Dosatron International, Inc.

The solution may be delivered to the plant tissue by standard pesticide application techniques. High volumes may be applied by hydraulic spraying and low volumes may be applied by misting or fogging. The solution may also be applied by injecting the hydrogen peroxide into a commercial cooling system. Alternatively, the hydrogen peroxide may be injected into a recirculating subirrigation nutrient system solution to control microbial growth in the irrigation water.

The hydrogen peroxide solution may be applied to the plant tissue at a variety of stages in the plant production cycle. This is illustrated by ever present problem of *Botrytis cinerea* foliar and stem blight experienced in all zonal geranium propagation. By injecting hydrogen peroxide solution into the water that is misted over the terminal stem cuttings until they reach root sufficiency surface microbial contaminants, including most notably Botrytis, will be reduced. This will dramatically reduce the cost of propagating this crop by reducing plant modality, plant handling and fungicide applications.

Another unexpected result of the field trials with the hydrogen peroxide product was the lethal effect it had upon the insect pest that were present in the greenhouse. The insect pests that were adversely affected by the peroxide treatment were, mealy bug, aphids, spider mites, white fly, fungus gnats, and thrip. The effects of the hydrogen peroxide appear to be upon the embryonic stages of the insects except for fungus gnats which disappeared probably because of the removal of the fungus in the greenhouse which is their source of food. Because of the short life time of most insects and the vulnerability of insects in the embryonic stages the treatment is highly effective.

The use of the method in accordance with the present invention is illustrated by the following examples:

EXAMPLE #1

The effectiveness of hydrogen peroxide in reducing the activity of *Botrytis cinerea* on the surface of zonal geranium cuttings during mist propagation can be seen by referring to Table 1. In this study 500 zonal geranium cuttings were treated with a mist during the entire course of their propagation. One mature leaf from each of 10 terminal stem cuttings following treatment were sampled and the data was averaged.

TABLE 1

|  | TREATMENT | MICROORGANISMS/ LEAF |
| --- | --- | --- |
| Control Group | 1.00% Water | 38,679 |
| Hydrogen Peroxide | 0.05% Hydrogen Peroxide | 38 |

The present invention contemplates the use of the method in accordance with the present invention on any type of plant material and virtually any known method of application of a such solution. The limitations to be considered are (1) the concentration must not be so great as to cause burning of the plant tissue and (2) the equipment used for application must have all parts of the application equipment in contact with the solution be constructed of materials that are compatible with the solution.

EXAMPLE #2

Roses in four different greenhouses were each sprayed at least four times with a 1% Hydrogen Peroxide solution. To insure objectivity, the greenhouses selected were not all commonly owned and many varieties of roses were included in the testing. The applications killed or seriously reduced the total mold count, including Botrytis and those molds causing Powdery Mildew. The effectiveness of the spray was measured by microbial culture of the surfaces of the greenhouse and the leaf surfaces of the treated and untreated plants. After the first application of the 1% hydrogen peroxide mixture the treated plants and surfaces were almost 100% free of total fungi as measured by the microbial culture methods. It is well known that these fungi are airborne. Thus, without further corrective action re-contamination of the environment is expected. Subsequent daily applications of a 500 PPM (parts per million) hydrogen peroxide mixture were made over the course of several weeks. During that time no re-contamination by fungi occurred as determined by the microbial culture method. No adverse effects were noted upon the plants after six weeks of observation.

EXAMPLE #2

The treatment of the greenhouses in Example #1 resulted in the destruction of the larval stages of the mealy bug, white fly, aphids, spider mites, and thrip. Also eliminated, were fungus gnats, probably due to the removal of their food source.

EXAMPLE #3

Hydrogen peroxide was introduced into the cut flower water solution at the rate of 500 PPM to keep the flowers fresh after harvest. A comparison was made with the various commercial products available for this purpose. Drooping of the necks, clarity of the water, color of the flowers, and general all-over appearances were observed for a period of two weeks. Additional water was added to all containers as needed. The hydrogen peroxide containers remained clear through the period and all flowers remained in excellent condition with only slight neck droop observed. The commercial products were about 50–75% as effective as the hydrogen peroxide.

EXAMPLE #4

A dilute solution of hydrogen peroxide was introduced into the misting system used on a rooting bench where cuttings of plants are placed in rooting medium and kept moist until roots are produced. Prior to sticking the cuttings in the rooting medium the cutting were dipped in 0.5% hydrogen peroxide. This procedure virtually eliminated cutting loss due to root rot and other infectious pathogens that can claim up to 50% of untreated cuttings

EXAMPLE #5

In the cut flower industry, the moist flowers are wrapped in plastic prior to placement in the shipping boxes for transit. Ice is added to the boxes in many cases to help keep the flowers fresh during transit. This closed, moist environment is very conducive to Botrytis and Black Spot Mold. Wetting the flowers with a dilute solution of hydrogen peroxide prevented and or delayed the appearance of the detrimental fungi. The addition of hydrogen peroxide to the water supply producing the ice also insured a slow release of hydrogen peroxide throughout the transit time.

EXAMPLE #6

The wooden boxes used for the transportation of cut roses can be a source of contamination. Chemical disinfection of the wooden boxes is difficult due to the porous nature of the wood. Chemical disinfectants are prone to leaving a residual in the wood which can be harmful the fragile flowers. Sanitizing with a 1% solution of hydrogen peroxide proved very effective, leaving no residue and aiding in the removal of many stains due the reuse of the boxes.

Other testing has shown that hydrogen peroxide will kill algae in pools of water. Thus, the treatment with hydrogen peroxide in accordance with the present invention will still further reduce the incidence of infections diseases by eliminating algae that may develop in the irrigation water or other pools of water that may develop in the vicinity of the plants to be protected.

It will be further understood that the example #3 referred to above that relates to cut flowers is representative of a still broader application of the present invention. More specifically, immersion of fruit such as peaches into a hydrogen peroxide solution will control both bacteria and fungi on the fruit and will thus dramatically increase shelf life. Advantageously, the hydrogen peroxide breaks down into hydrogen and oxygen and leaves no residue on the produce. The implications of this aspect of the invention are as dramatic for (1) cultivation of food products and preservation of food products and cuttings of food product plants as it is for (2) cultivation of ornamental plants and preservation of ornamental plant cuttings. It will be understood that the term "plant tissue" as used herein is intended to include plants produced for food, the fruit of such plants, plants produced for ornamental purposes and the cuttings of both ornamental plants and plants produced for food.

Anther benefit of the use of hydrogen peroxide was observed in the addition of low concentrations (50–100 PPM) into ornamental pools of recirculated water to keep the water clear and free of bacteria and algae. In fact, treatment of algae infested water with hydrogen peroxide killed the algae and cleared the water. The low concentration of the hydrogen peroxide demonstrated no adverse effect upon the fish (usually Gold Fish). The solution of hydrogen peroxide, when mixed with a dilute solution of acetic acid and a small amount of surfactant, was very effective on the affected surfaces of greenhouse environments and plants. The usual formulation was:

| Active Agent | Hydrogen Peroxide | 1.00% |
|---|---|---|
| Stabilizer | Acetic Acid | 0.05% |
| Enhancing Agent | Soap or Detergent | 0.15% |

A simple dilution of 50–100 PPM of hydrogen peroxide with no additives was used in the ornamental pools when fish were present.

In another evaluation hydrogen peroxide was introduced into a recirculating ornamental pool at the rate of 100 PPM. The algae already present in the water was killed and sunk below the surface of the water within 24 hours. Keeping the level of hydrogen peroxide in the 50–100 PPM range prevented a resurgence of the algae. The treatment had no adverse effect upon the goldfish residing in the pool.

The disclosed method achieves four of the five principles of control by a single procedure. Resistance by genetic mutation is not affected since no evidence was developed that hydrogen peroxide is a mutagen.

The invention has been described with reference to its illustrated preferred embodiment. Persons skilled in the art of such devices may upon exposure to the teachings herein, conceive other variations. Such variations are deemed to be encompassed by the disclosure, the invention being delimited only by the following claims.

Having thus described my invention we claim:

1. The method for control of horticulture diseases in living plants and decontamination of living plant tissue which comprises:

spraying a solution including but not limited to hydrogen peroxide in the liquid phase to a part of a plant above the root of the plant, said hydrogen peroxide being a solution having a concentration of between 0.05 to 3.00%.

2. The method as described in claim 1 wherein:
   the hydrogen peroxide solution has a concentration of between 0.05 and 1.5%.

3. The method as described in claim 1 wherein:
   the hydrogen peroxide solution is applied by hydraulic spraying.

4. The method as described in claim 1 wherein:
   the hydrogen peroxide solution is applied by misting.

5. The method as described in claim 1 wherein:
   the hydrogen peroxide solution is applied by fogging.

6. The method as described in claim 1 wherein:
   the hydrogen peroxide solution is applied to the plant tissue at a variety of stages in the plant production cycle.

7. The method as described in claim 1 wherein:
   the hydrogen peroxide solution is injected into the water that is misted over terminal stem cuttings until they reach root sufficiency.

8. The method as described in claim 1 further including:
   the step of separating a piece of the part of the plant from the rest of the plant before spraying the piece.

9. The method as described in claim 8 wherein:
   said piece is a stem cutting.

10. The method as described in claim 8 wherein:
    said piece is a produce product.

11. The method as described in claim 8 wherein:
    said piece is a cut flower product.

12. The method as described in claim 1 further including:
    the step of separating a piece of the part of the plant from the rest of the plant before spraying the piece.

13. The method as described in claim 12 wherein:
    said piece is a stem cutting.

14. The method as described in claim 12 wherein:
    said piece is a produce product.

15. The method as described in claim 12 wherein:
    said piece is a cut flower product.

16. The method for control of horticulture diseases and decontamination of plant tissue which comprises:

spraying a solution including but not limited to hydrogen peroxide and acetic acid in the liquid phase to a part of a plant above the root of the plant, said hydrogen peroxide within said solution having a concentration of between 0.05 to 3.00%.

17. The method as described in claim 16 wherein:
    the hydrogen peroxide has a concentration within said solution between 0.05 and 1.5%.

18. The method as described in claim 16 wherein:
    the hydrogen peroxide solution is applied by hydraulic spraying.

19. The method as described in claim 16 wherein:
    the hydrogen peroxide solution is applied by misting.

20. The method as described in claim 16 wherein:
    the hydrogen peroxide solution is applied by fogging.

21. The method as described in claim 16 wherein:
    the solution is applied to the plant tissue at a variety of stages in the plant production cycle.

22. The method as described in claim 16 wherein:
    the hydrogen peroxide in the solution has a concentration of between 0.05 and 1.5%.

23. The method for control of horticulture diseases in living plants and decontamination of living plant tissue which comprises:

spraying a solution including but not limited to hydrogen peroxide and an acid selected from the group consisting of acetic acid and phosphoric acid in the liquid phase to a part of a plant above the root of the plant, said hydrogen peroxide having a concentration within the solution of between 0.05 to 3.00% and said acid selected from the group consisting of acetic or phosphoric acid having a concentration in the solution of about 0.05%.

24. The method as described in claim 23 further including:
    the step of separating a piece of the part of the plant from the rest of the plant before spraying the piece.

25. The method as described in claim 24 wherein:
    said piece is a stem cutting.

26. The method as described in claim 24 wherein:
    said piece is a produce product.

27. The method as described in claim 24 wherein:
    said piece is a cut flower product.

* * * * *